US007172995B1

(12) United States Patent
Klingner

(10) Patent No.: US 7,172,995 B1
(45) Date of Patent: Feb. 6, 2007

(54) METHOD FOR MINIMIZING ABSORPTION OF AND EFFECTING REMOVAL OF CONTAMINANT CHEMICALS

(75) Inventor: Thomas D. Klingner, Prospect Heights, IL (US)

(73) Assignee: Colormetric Laboratories, Inc., Des Plaines, IL (US)

( * ) Notice: Subject to any disclaimer, the term of this patent is extended or adjusted under 35 U.S.C. 154(b) by 341 days.

(21) Appl. No.: 10/712,899

(22) Filed: Nov. 14, 2003

Related U.S. Application Data

(63) Continuation-in-part of application No. 09/871,187, filed on May 31, 2001, now Pat. No. 6,670,313.

(60) Provisional application No. 60/209,499, filed on Jun. 5, 2000.

(51) Int. Cl.
*C11D 3/44* (2006.01)

(52) U.S. Cl. ...................... 510/130; 510/137; 510/138; 510/157; 510/159; 510/407; 424/59

(58) Field of Classification Search ..................... None
See application file for complete search history.

(56) References Cited

U.S. PATENT DOCUMENTS 3,795,624 A 3/1974 Feinstone
4,239,781 A 12/1980 Edwards
4,496,357 A 1/1985 Osburn
4,533,545 A 8/1985 Sebag
4,913,897 A * 4/1990 Chvapil et al. ............... 424/59
4,968,448 A 11/1990 Svarz
5,140,986 A * 8/1992 Klingner ..................... 600/367
5,202,357 A 4/1993 Bowser et al.
5,308,526 A 5/1994 Dias et al.
5,462,691 A 10/1995 Shimada et al.
5,558,806 A 9/1996 Policello et al.
5,632,727 A * 5/1997 Tipton et al. ................. 602/47
5,703,104 A * 12/1997 Peck et al. .................. 514/369
5,725,491 A * 3/1998 Tipton et al. ................. 602/43
5,763,386 A 6/1998 Mondin et al.
5,792,469 A * 8/1998 Tipton et al. ............... 424/422
5,792,739 A 8/1998 He et al.
5,798,330 A 8/1998 Misselyn et al.
5,811,107 A 9/1998 Gangadharan et al.
5,837,274 A 11/1998 Shick et al.
5,837,661 A 11/1998 Evans et al.
5,856,284 A 1/1999 Hamada et al.
5,871,764 A 2/1999 Diaz et al.
5,882,666 A 3/1999 Averill et al.
5,891,449 A 4/1999 Daniel et al.
6,086,905 A * 7/2000 Peck et al. .................. 424/406
6,670,313 B1 * 12/2003 Klingner ..................... 510/130

OTHER PUBLICATIONS

"In Vivo Evaluation of MDI Skin Decontamination Procedures," Wester et al., Polyurethanes Expo '98 (1998).
"Evaluation of Compounds as Barriers to Dermal Penetration of Organophosphates Using Acetylcholinesterase Inhibition," Olson et al. Toxicology Letters, 55, pp. 325-334 (1991).

* cited by examiner

*Primary Examiner*—Gregory Webb
(74) *Attorney, Agent, or Firm*—Seyfarth Shaw LLP

(57) ABSTRACT

A person's skin is protected from percutaneous absorption of lipophilic or semi-polar contaminant chemicals by applying to the skin, before the skin is wetted with water, a plural-constituent solvent system having an average molecular weight greater than or equal to 350 and including at least one solvent in which the contaminant chemicals are soluble. The solvent system may be applied to the skin before exposure to serve as a barrier, or may be applied to the skin or other surface after exposure to serve as a cleanser. The solvent system may include one or more emulsifiers and/or reactive chemical deactivation agents, and/or organic pH modifiers, and/or UV blockers, and/or insect repellents. Oil-based and glycol-based solvent systems are disclosed, each having at least two solvents which may have different solubility ranges. The solvent system includes no water, emollients or detergents and all constituents are skin-safe.

23 Claims, No Drawings

METHOD FOR MINIMIZING ABSORPTION OF AND EFFECTING REMOVAL OF CONTAMINANT CHEMICALS

RELATED APPLICATIONS

This application is a continuation-in-part of U.S. application Ser. No. 09/871,187, filed May 31, 2001 now U.S. Pat. No. 6,670,313 which, in turn, claims the benefit of the filing date of U.S. provisional application No. 60/209,499, filed Jun. 5, 2000.

BACKGROUND

This invention relates to techniques for minimizing percutaneous absorption of toxic chemicals and for effective removal of toxic chemicals from skin or other surfaces exposed to the chemicals.

Skin exposure to toxic chemicals has long been a problem. To prevent skin exposure to chemicals, gloves or other protective clothing have been worn. Such gloves, however, are cumbersome to wear and have caused allergic reactions and other problems.

Heretofore, when non-protected skin was contacted with harmful toxic chemicals ("contaminant chemicals"), the skin would typically be flushed with copious amounts of water or with soap and water (as routinely recommended by most material safety data sheets) to try to cleanse the skin of the contaminant chemical and prevent percutaneous absorption thereof. Though this may have been useful for skin exposed to hydrophilic chemicals, it was not efficient for removing from the skin chemicals which are not soluble in water (lipophilic) or only slightly soluble in water (semi-polar). In fact, rinsing with water may actually increase the percutaneous absorption of such chemicals.

Percutaneous absorption and systemic absorption of chemicals is a two step process. The first step is the initial partitioning of a lipophilic chemical into the lipid components in the stratum corneum. This initial absorption can be relatively rapid if the chemical is a strong solvent and of low molecular weight. The process will move more slowly if the chemical is a higher molecular weight or less lipid soluble.

The second step in the systemic absorption process is the partitioning of the chemical from the lipophilic components of the skin into the hydrophilic bloodstream. This process can be quite slow as the preferential solubility of the chemical in the stratum corneum lipids serves to retain the chemical in the skin. This absorbed dose of chemical in the skin is referred to as the skin depot.

The use of water to first wet the skin when attempting to remove toxic lipophilic chemicals has two detrimental effects which can result in an enhancement of percutaneous exposure. First, due to the poor solubility of these chemicals in water, the use of water can spread chemical contamination over a greater surface area of the skin. Thus, percutaneous exposure to the chemical can increase.

Secondly, the application of water to the skin results in a rapid hydration and saturation of the corneocytes (dead skin cells constituting the stratum corneum). The lipophilic chemical already absorbed into the skin's lipids (skin depot) is now presented with a very different solubility environment. Where a lipophilic chemical previously demonstrated a higher preferential solubility in the skin lipids as opposed to the hydrophilic bloodstream; the hydration of the skin with water now shifts the skin to a hydrophilic state. Thus, the absorbed chemical is more rapidly absorbed into the body as its solubility in the skin decreases. Partitioning into the bloodstream now becomes concentration rather than solubility dependent.

Therefore, the use of water or soap and water can increase the area of skin exposure and cause a more rapid systemic absorption of the chemical into the bloodstream.

Though it is known that common lipophilic chemicals are more soluble in lipophilic solvents than water, the application of common lipophilic solvents to the skin to remove contaminant chemicals therefrom has not been successful because, as discussed below, these solvents penetrate or diffuse across the skin and allow the contaminant chemical to be carried across the skin barrier.

The ability of a chemical to be absorbed through the skin depends on two primary chemical characteristics, its solubility relative to water and its molecular size.

The outermost layer of the skin, the stratum corneum, consists mainly of highly keratinized dead skin cells held together by interstitial layers of lipids. The primary function of the stratum corneum is to retain moisture in the body and provide a physical barrier to infectious bacteria and viruses. Thus, the skin is a highly effective barrier to the absorption or loss of water and water soluble (hydrophilic) chemicals.

The ability, or lack thereof, of a chemical to partition into the stratum corneum is the initial limiting step in determining the dermal penetration rate (Kp). Since like materials dissolve like materials, the stratum corneum is most permeable to fat soluble (lipophilic) chemicals because of its layers of lipids.

The second characteristic determining the dermal penetration rate (Kp) is the molecular size of the chemical contaminant. Molecular size generally increases with the molecular weight (MW) of the chemical. Chemicals with high molecular weights, such as those greater than 350, are significantly limited in their ability to permeate the stratum corneum due to their physical size, while lower molecular weight chemicals more easily permeate the stratum corneum.

Thus, low molecular weight lipophilic chemicals that are insoluble or poorly soluble in water are readily absorbed through the skin.

Solvents for removing contaminant chemicals from the skin should be chosen based on their ability to dissolve those chemicals. The solubility of a chemical in a solvent is determined by it octanol/water partition coefficient (log K o/w). Solvents with a log K o/w value similar to that of a contaminant chemical will readily dissolve the chemical.

An appropriate solvent is important because the partition coefficient of a contaminant chemical, Ksc/Kv (Ksc, solubility in the stratum corneum, vs Kv, solubility in the solvent), defines the equilibrium ratio of the concentration of the compound in the stratum corneum to that in the adjacent application solvent (trying to dissolve the chemical). Therefore, a contaminant chemical with a higher affinity (solubility) for a solvent that is applied on the skin will partition more slowly into the stratum corneum. Therefore, one would believe that solvents which readily dissolve a contaminant chemical would, when applied to skin contacted with the contaminant, dissolve the contaminant chemical and limit percutaneous absorption thereof.

This concept, however, is valid only if the solvent itself does not affect the absorption properties of the skin (damage the stratum corneum) and if the solvent itself does not diffuse across the stratum corneum. If the solvent does diffuse across the stratum corneum, it acts as a carrier or active transport of the contaminant chemical being absorbed. Therefore, though a contaminant chemical may have a much higher solubility in a low molecular weight lipophilic solvent than in the stratum corneum, the low molecular weight lipophilic solvent could not be used to prevent percutaneous absorption of the chemical because the low molecular weight lipophilic solvent would be absorbed into the stratum corneum and act as a carrier for the chemical.

Disrupting the stratum corneum significantly increases the percutaneous absorption of chemical exposure, thereby contributing to the development of irritant or allergic dermatitis. Thus, skin cleansers incorporating harsh detergents which can damage the skin tend to increase the potential for skin absorption of chemical exposure. The addition of cosmetic emollients or "moisturizers" to such cleansers can further promote chemical absorption. Commonly used additives, such as aloe vera and isoproplymyristate are rapidly absorbed into the stratum corneum. Moreover, these additives have been proven to be effective vehicles to enhance the absorption efficacy of lipohilic drugs. D-limonene, widely employed in citrus-based skin cleansers, has been shown to be among the most effective penetration enhancers for dermal drug delivery.

Thus, to date, there have been no completely satisfactory methods for minimizing the percutaneous absorption of lipophilic or semi-polar chemicals which have been in contact with the skin.

OSHA also recognized that there have been no such satisfactory methods. On Aug. 10, 1992, OSHA promulgated a final rule, 29 CFR, parts 1910 and 1926, Occupational exposure to 4,4' methylenedianiline (MDA). OSHA recognized in assessing exposure risk that "in certain situations approximately 95% of exposure results from dermal absorption." OSHA further stated "MDA cannot be completely removed by cleansing. The data suggest that the use of solvents to remove MDA from the skin actually increases the absorption of MDA. It also appears that soap and water provide the best medium for removing the substance from the skin but only removes 60% of the material deposited on the skin."

The final standard requires that "workers subjected only to dermal exposure to MDA must be instructed to immediately wash exposed areas with soap and water or any medium which does not increase the absorption properties of MDA. This particular requirement was given much consideration by OSHA."

The comments to the rule make it clear that OSHA did not want to require that only soap and water be used to remove MDA impregnated resin or accumulations on the skin because something better might be developed in the future. OSHA believed that if a particular solvent could be demonstrated not to increase the absorption properties of MDA it should be used to remove MDA from the skin. OSHA, did not, however, suggest any such solvent.

The same chemical principles of solubility apply to the decontamination of chemicals from surfaces of personal protective clothing or equipment (PPE), gloves, suits, respirators, etc. Many items of protective clothing or other equipment may be quite expensive and, therefore, are not discarded after use. It is common practice for firefighters or emergency response personnel, after being exposed to toxic chemicals, to wash their gear with a water rinse shower before removal. This act of apparent decontamination provides a false sense of security that the protective gear is free from contamination during removal and storage. A recent study demonstrated that 90% of workers contaminated their hands when removing and then re-using exposed gloves. Although in this study there was no attempt to decontaminate the gloves prior to removal, standard practices of a water rinse would have invariably left contamination. Ineffective decontamination of PPE may increase exposures if the workers falsely believe their protective equipment is clean. It is therefore apparent that improvements over the standard use of soap and water to decontaminate skin and protective equipment from toxic lipophilic chemicals will significantly improve worker safety.

Sometimes, in certain industrial environments and the like, over time deposits of contaminant materials may build up on a worker's protective equipment, such as gloves. When this occurs, it is known for the worker to simply dip the gloves into a suitable solvent for removing the contaminant material. However, such solvents, particularly if they are of low molecular weight, may be able to penetrate the glove surface and actually serve as a carrier for the contaminant material to the inside of the glove.

SUMMARY

This application discloses improved techniques for minimizing percutaneous absorption of contaminant chemicals exposed to the skin and for removing contaminant chemicals from skin or other exposed surfaces, which avoid the disadvantages of prior techniques.

An important aspect is the provision of a method which does not involve first wetting with water a surface subject to exposure to contaminant chemicals.

Another aspect is the provision of a method of the type set forth, which includes applying to the skin or contaminated surface a solvent system which is comprised essentially entirely of high-molecular-weight compounds which have limited ability to diffuse through the skin or other exposed surface.

Yet another aspect is the provision of a method of the type set forth, which utilizes a solvent system in which the contaminant chemical has a high solubility.

Still another aspect is the provision of a method of the type set forth, which utilizes a solvent system which can be rinsed from an exposed surface with water.

A still further aspect is the provision of a method of the type set forth, wherein the solvent system includes an emulsifier.

Another aspect is the provision of a method for effectively removing contaminant chemicals from a surface exposed to the chemicals.

Another aspect is the provision of a method of the type set forth, in which the solvent system eliminates the use of water, emollients, and detergents.

A further aspect is the provision of a method of the type set forth which minimizes damage to the skin.

Certain ones of these and other aspects may be attained by the method of inhibiting percutaneous absorption of a contaminant chemical on a person's skin comprising: applying to the person's skin a non-aqueous solvent system including plural skin-safe constituents each having a molecular weight of at least 350, the constituents including at least one solvent in which the contaminant chemical is soluble.

The disclosed methods consist of certain novel features and a combination of steps hereinafter fully described, it being understood that various changes in the details may be made without departing from the spirit, or sacrificing any of the advantages of the subject matter sought to be protected.

DETAILED DESCRIPTION

This application discloses a method and composition to minimize absorption of non-polar (lipophilic) and semi-polar chemicals by applying a non-aqueous, high molecular weight ("HMW") solvent system to the skin as a barrier prior to exposure to the chemicals and/or as a cleansing solution for skin or other surfaces after exposure to the chemicals. The solvent system has an average molecular weight of at least 350. In particular, the solvent system is formed essentially of all HMW, skin-safe constituents, each having a molecular weight of at least 350, and preferably greater than 400. These HMW chemicals, as discussed above, have little ability to permeate the stratum corneum. The method is especially useful in minimizing or preventing the percutaneous absorption of industrial chemicals, such as aromatic amines, isocyanates, pesticides, oils, grease, paints and the like, but may have wider application, such as preventing percutaneous absorption of chemical warfare agents. Preferably, at least about 75 weight % of the solvent system is formed of HMW constituents, and most preferably as close to 100 weight % as possible. Each solvent system is specifically formulated to be able to optimally dissolve predetermined contaminant chemicals in contact with the skin or other exposed surface to efficiently remove non-polar and semi-polar chemicals from the such surfaces while minimizing deleterious effects to the skin's natural barrier function. In this regard, solvent systems are formulated to dissolve chemicals within a range of octanol/water partition coefficients (log K o/w). Thus, individual solvent systems can be formulated to best dissolve lipophilic chemicals with a high log K o/w or can be formulated to best dissolve chemicals having a lower log K o/w. The solvent systems are also formulated to be able to be rinsed from the skin or other exposed surface with water and may, accordingly, include a HMW emulsifier. Examples of solvent systems for minimizing percutaneous absorption of and facilitating removal of lipophilic and semi-polar chemicals are discussed below.

Oil-Based Lipophilic (Non-Polar) Solvent Formulation

To remove highly lipophilic (log K o/w>3.0) chemicals from the skin or other exposed surface, a liquid or semi-solid solvent system ("oil-based solvent system") is applied to the surface. The oil-based solvent system is comprised of skin-safe constituents each having a molecular weight of at least 350, and preferably greater than 400, and which is formulated to be able to dissolve these lipophilic chemicals. The oil-based solvent system preferably has a maximum solubility for chemicals with a log K o/w in the range of from about 4.5 to about 6.5.

The solvent system is preferably comprised of a first solvent, such as one or more triglycerides (preferably one or more natural plant oils) and/or a methyl ester of a high-molecular weight fatty acid (C22 or greater, such as high euricic acid rapeseed oil); a second solvent, such as polypropylene glycol (average molecular weight of at least 350) or a similar solvent, such as a polyalkoxylated polyether or block polyol, and one or more emulsifiers (preferably non-ionic food or cosmetic grade) to enable the oil-based solvent system to be rinsed from the skin with water. Non-active additives, such as preservatives, stabilizers, viscosity modifiers, fragrance and colorants can be included for appearance and shelf life.

Preferred plant oils include soybean, corn, olive, canola, cotton seed, sunflower or other common plant oils, in either their natural or hydrogenated form. The triglyceride(s) comprises from about 10 to about 90 weight %, preferably from about 30 to about 70 wt. %, of the solvent system.

The second solvent is preferably less lipophilic than the plant oil to broaden the solubility range of the solvent system. Preferred second solvents include polypropylene glycols (having an average molecular weight of from about 350 to about 2000, preferably from about 425 to about 700) and polyester or polyether based solvents. The second solvent preferably comprises from about 10 to about 70 weight % of the oil-based solvent system, and more preferably from about 20 to about 45 wt. %.

Preferred emulsifiers include any of a range of common non-ionic surfactants having a molecular weight of at least 350, including food grade emulsifiers such as polyoxyethylene sorbitan esters (polysorbates), sorbitan esters, polyoxyethylene ethers, polyhydric alcohol esters, polyethylene glycol esters or glycerol esters. The emulsifiers enhance the water rinseability of the oil-based solvent system. Preferably, the emulsifier comprises from about 2.5 to about 20 weight % of the solvent system.

Examples of the oil-based solvent system are set forth below:

Example 1

| Component | Weight % |
|---|---|
| Soybean oil | 55 |
| Polypropylene Glycol (MW 700) | 30 |
| PEG 400 Dioleate | 10 |
| PEG 400 Monooleate | 5 |

| Component | Weight % |
|---|---|
| Example 2 | |
| Corn oil | 55 |
| Polyalkoxylated polyether (Macol 625) | 35 |
| Plysefbate Polysorbate 85 | 7.5 |
| PEG 400 Dioleate | 7.5 |
| Example 3 | |
| high euracic acid rapeseed oil | 50 |
| methyl ester | 30 |
| polypropylene glycol | 30 |
| (avg. molecular weight 425) | 5 |
| polysorbate 80 | 10 |
| polyethylene glycol 400 dioleate | 10 |

These oil-based solvent systems are effective in removing harmful chemical contaminants having a log K o/w exceeding 3.0, such as toluene diisocyanate, benzo-a-pyrene, methylene bis phenyl diisocyanate, pentachlorophenol, chlorpyrifos, polychlorobenzenes, DDT, diesel oil, parathion, toluene, benzene, aldrin, lindane and malathion.

Glycol Based (Semi-Polar) Solvent System Formulation

A liquid or semi-solid solvent system for the removal of semi-polar (log K o/w-0.5 to 4.0) chemical species ("semi-polar solvent system") from the skin or other exposed surface has an average molecular weight of at least 350 and, preferably, is comprised of skin-safe constituents each having a molecular weight of at least 350, and preferably greater than 400, and which system is formulated to be able to dissolve these semi-polar chemicals. The semi-polar solvent system preferably has a maximum solubility for chemicals with a log K o/w from about 1.5 to about 2.5. The semi-polar solvent system preferably includes polyethylene glycol (PEG), polypropylene glycol (PPG) and one or more surfactant emulsifiers. The semi-polar system can also include non-active additives to affect appearance or shelf life of the semi-polar solvent system.

The preferred average molecular weight of the PEG is from about 350 to about 1500. Below 350, the smaller molecular size results in increased percutaneous absorption. Above molecular weight 1500, the PEG is a viscous solid limiting its solvent action. The PEG comprises from about 20 to about 80 weight %, preferably from about 40 to about 70 weight %, of the semi-polar solvent system.

The preferred average molecular weight of the PPG is from about 425 to about 2000. Above a molecular weight of 500, PPG become increasingly water insoluble (lipophilic). This increasingly non-polar character limits its solvency function of semi-polar chemicals. PPG comprises from about 10 to about 60 weight %, preferably from about 20 to about 40 weight % of the solvent system.

Other chemical solvents, such as polyalkoxylated polyethers and block polyols may be used in place of or in addition to PEG and PPG, to change the solvent system's log K o/w or solubility characteristics needed to dissolve the contaminant chemical(s).

The semi-polar solvent system also includes one or more surfactant emulsifiers, preferably non-ionic or mild high-molecular-weight ionic species to improve water rinseability and solvent function. The preferred surfactant emulsifiers have a molecular weight of at least 350, preferably greater than 400, and may be non-ionic surfactants, such as polysorbates, polyoxyethylene ethers, polyethylene glycol esters and block polymers, or mild ionic surfactants. The surfactant emulsifier comprises from about 5 to about 30 weight %, preferably about 10 weight % of the semi-polar solvent system.

Examples of several semi-polar solvent system formulations are below:

| Component | Weight % |
|---|---|
| Example 4 | |
| PEG 400 | 50 |
| PPG 425 | 40 |
| Polysorbate 80 | 5.0 |
| PEG 400 Monooleate | 5.0 |
| Example 5 | |
| PEG 400 | 30 |
| PEG 600 | 15 |
| PPG 425 | 25 |
| PPG 700 | 15 |
| Polysorbate 60 | 7.5 |
| PEG 400 Dioleate | 7.5 |
| Example 6 | |
| PEG 400 | 60 |
| Polyalkoxylated polyether (Macol 660) | 30 |
| PEG Monolaurate | 10 |

The semi-polar based solvent system is effective in removing harmful chemical contaminants with a log K o/w from about −0.5 to about 4, such as aldrin, lindane, malathion, aniline, dinitrotoluene, nitroaniline, trinitrobenzene, dichloroethane, captan, methylenebischloroaniline, methylenedianiline, phenol, acrylonitrile and acetone.

Use of the Solvent Systems

When a person's skin or other exposed surface, such as a surface of protective clothing or equipment, is contacted with a contaminant chemical, an appropriate HMW solvent system, described above, which will dissolve the chemical is applied to the affected area of the surface before the surface is wetted with water. The solvent system is then simply rinsed off with water. After the surface has dried, the solvent system can be reapplied and rinsed off again as necessary. Gentle rubbing or physical agitation of the exposed surface during application of the solvent may enhance even contact and mixing with the contaminant chemical and assures maximal solubilization of the toxic chemical into the solvent. Only after this critical first step is water used to rinse the chemical from the skin or other surface.

Alternatively, the solvent system can be used as a barrier and applied to the person's skin prior to the person using or coming in contact with dangerous chemicals. The appropriate solvent system is chosen based upon the log K o/w of the chemicals to which a user will be exposed. When a dangerous chemical contacts the skin, the solvent system is washed off with water, and reapplied, as necessary.

The initial step in the percutaneous absorption of non-aqueous chemicals is the partitioning of the chemical into the skin lipids. The application of HMW solvent layer to the skin prior to chemicals exposure will significantly inhibit the initial partitioning of the chemical into the stratum corneum, thus limiting the formation of an absorbed skin depot.

The initial partitioning into the skin lipids is a solubility driven process i.e. the lipophilic chemical is preferentially soluble in the lipid structure of the skin. Pre-exposure application of a non-absorbing HMW lipophilic solvent to the skin's outer surface modifies the exposure kinetics. The lipophilic contaminant is now presented to the stratum corneum in an environment where it is more soluble than the contaminant's solubility in the skin. Therefore, the initial partitioning shifts away from the skin toward the solvent. The rate of percutaneous absorption now shifts from a solubility driven process to a concentration driven process (Fick's Law). Therefore, as the concentration of the chemical contaminant on the skin exceeds the solubility capacity of the solvent, absorption into the skin lipids will be driven by said excess chemicals concentration.

Thus, ideally, to minimize percutaneous absorption of chemical contaminants, it may be desirable that the barrier solvent be periodically removed (rinsed off) and a new barrier layer applied. The frequency of this barrier layer renewal will depend on the concentration and frequency of contaminant exposure and the relative solubility capacity of the barrier solvent for the contaminant vs the solubility of the contaminant in the skin lipids.

Reactive Deactivation

The primary determinants of toxicological concern are the level of exposure and the toxicity of the chemical contaminant. Thus high exposures to a chemical of low toxicity may be of less concern than a low level exposure to a highly toxic contaminant.

The addition of specific reactive chemical deactivation agents to the HMW solvent formula can function to transform a highly toxic contaminant into a much less toxic chemical reaction product. An example would be the well known oxidative deactivation of organophosphate cholinesterase inhibitor pesticides and chemical nerve agents.

Current recommendations for decontaminating victims of a chemical nerve agent exposure (sarin, VX, etc) is to wash the skin or other exposed surface with a bleach solution.

Bleach, sodium hypochlorite, is a strong oxidizer and is intended to react with the nerve agents, thereby deactivating them. Dilute bleach solutions are corrosive to the skin and only minimally effective in reacting with nerve agents. The primary reason for the poor efficacy of bleach is that bleach is a water soluble chemical. In additional to all of the prior mentioned problems of applying water to a lipophilic contaminant, the oxidative deactivation reaction is ineffective because the organophosphate nerve agent is not co-soluble with the sodium hypochlorite.

The addition of a skin safe organic oxidizer, such as benzoyl peroxide, to the HMW solvent formulation would significantly improve the oxidative deactivation reaction. In addition, all prior benefits of the HMW solvent method would enhance the decontamination or barrier functions as previously described.

pH Effect

The pH (acid/basic) of the skin exposure environment can profoundly affect the rate of percutaneous absorption for certain chemicals. Addition of a pH modifier, such as an organic acid or base, to the HMW solvent formula can adjust the skin exposure environment, resulting in reduced percutaneous uptake.

Other Constituents

UV radiation from sunlight damages the protective barrier function of the skin, thereby resulting in enhanced dermal absorption of chemicals. The addition of UV blockers to the HMW solvent formulation would enhance its performance when utilized as a protective barrier in sunlight. Additionally, when used out of doors as a barrier to chemical exposure to such toxic chemicals as pesticides, herbicides, creosote, etc., an approved insect repellent. such as DEET, can be added to the HMW solvent formulation with no significant deleterious effect on its barrier function, while providing the benefit of an insect repellent.

The matter set forth in the foregoing description is offered by way of illustration only and not as a limitation. While particular embodiments have been described, it will be apparent to those skilled in the art that changes and modifications may be made without departing from the broader aspects of applicants' contribution. The actual scope of the protection sought is intended to be defined in the following claims, when viewed in their proper perspective based on the prior art.

What is claimed is:

1. The method of inhibiting absorption into a person's skin of a contaminant chemical on the person's skin comprising:

applying to the person's skin a non-aqueous solvent system consisting of plural skin-safe constituents each having a molecular weight of at least 350, the constituents including at least one solvent in which the contaminant chemical is soluble, so that the contaminant chemical is preferentially dissolved in the solvent system and neither the solvent system nor the contaminant chemical is absorbed into the person's skin.

2. The method of claim 1, wherein the solvent system is applied to the person's skin before exposure to the contaminant chemical to serve as a barrier.

3. The method of claim 2, wherein the solvent system is applied to a person's skin which has not been wetted with water.

4. The method of claim 1, wherein the applying step includes applying a solvent system which includes a reactive chemical deactivation agent for deactivating the contaminant chemical.

5. The method of claim 1, wherein the applying step includes applying a solvent system which includes an organic pH modifier.

6. The method of claim 1, wherein the applying step includes applying a solvent system which includes an ultraviolet radiation blocker.

7. The method of claim 1, wherein the applying step includes applying a solvent system which includes at least one insect repellent.

8. The method of claim 1, wherein the solvent system is applied to the person's skin subsequent to exposure to the contaminant chemical for use in cleansing the contaminant chemical from the skin.

9. The method of claim 1, and further comprising rinsing the solvent system and any dissolved contaminant chemical from the skin with water.

10. The method of claim 9, wherein the applying step includes applying a solvent system which includes at least one skin-safe emulsifier having a molecular weight of at least 350.

11. The method of claim 1, wherein the applying step includes applying a solvent system including plural solvents having different solubility ranges.

12. The method of claim 11, wherein the solvent system applied is oil-based.

13. The method of claim 11, wherein the solvent system applied is glycol-based.

14. A method of decontamination of a contaminated surface exposed to a contaminant chemical, comprising:

applying to the contaminated surface a non-aqueous solvent system consisting of plural constituents each having a molecular weight of at least 350, the constituents including at least one solvent in which the contaminant chemical is soluble.

15. The method of claim 14, wherein the contaminated surface is human skin.

16. The method of claim 14, wherein the contaminated surface is the surface of protective clothing or equipment.

17. The method of claim 14, wherein the applying step is performed before the contaminated surface is wetted with water.

18. The method of claim 14, and further comprising: rinsing the solvent system and any dissolved contaminant chemical from the contaminated surface with water.

19. The method of claim 18, and further comprising: drying the rinsed contaminated surface and then reapplying the solvent system to the dried surface.

20. The method of claim 19, and further comprising: rinsing the reapplied solvent system and any dissolved contaminant chemical from the skin with water.

21. The method of claim 14, wherein the applying step includes applying a solvent system which includes plural solvents having different solubility ranges.

22. The method of claim 14, wherein the applying step includes gentle rubbing or physical agitation of the contaminated surface.

23. The method of inhibiting absorption into a person's skin of contaminant chemicals on the person's skin comprising:

applying to the person's skin an emollient-free non-aqueous solvent system for dissolving the contaminant chemicals, wherein the solvent system consists of (a) a skin-safe first solvent having an average molecular weight of at least 350 so as to minimize its skin permeability and a maximum solubility for first contaminant chemicals which have an octanol/water partition coefficient (log K o/w) in a first range, and (b) a skin-safe second solvent having an average molecular weight of at least 350 so as to minimize its skin permeability and a maximum solubility for second contaminant chemicals which have a log K o/w in a second range different from the first range, at least one of the first and second ranges being less than 3.5, so that the contaminant chemicals is preferentially dissolved in the solvent system and neither the solvent system nor the contaminant chemicals is absorbed into the person's skin.

* * * * *